United States Patent [19]

Nappholz et al.

[11] Patent Number: 5,423,868
[45] Date of Patent: Jun. 13, 1995

[54] DUAL CHAMBER PACEMAKER WHICH DETECTS, CONFIRMS AND TERMINATES PACEMAKER MEDIATED TACHYCARDIA

[75] Inventors: Tibor Nappholz, Englewood; Stephen R. Chinn, Denver; Matthew J. Gani, Lakewood, all of Colo.

[73] Assignee: Telectronics Pacing Systems, Inc., Englewood, Colo.

[21] Appl. No.: 226,462

[22] Filed: Apr. 12, 1994

[51] Int. Cl.⁶ ............................................. A61N 1/368
[52] U.S. Cl. ................................................... 607/14
[58] Field of Search ............................... 607/14, 9

[56] References Cited

U.S. PATENT DOCUMENTS

| | | | |
|---|---|---|---|
| 4,686,989 | 8/1987 | Smyth et al. | 607/14 |
| 4,712,556 | 12/1987 | Baker, Jr. | 607/14 |
| 5,253,644 | 10/1993 | Elmqvist | 607/14 |

Primary Examiner—William E. Kamm
Assistant Examiner—Scott M. Getzow
Attorney, Agent, or Firm—Gottlieb, Rackman & Reisman

[57] ABSTRACT

A dual-chamber pacemaker for confirming pacemaker mediated tachycardia (PMT) after initial detection. The minimum V-V pacing interval is extended to be slightly longer than the interval of the sensed atrial rate. If the A-V Delay intervals in successive cycles remain constant, as opposed to progressively increasing in Wenckebach fashion, then PMT is confirmed.

21 Claims, 4 Drawing Sheets

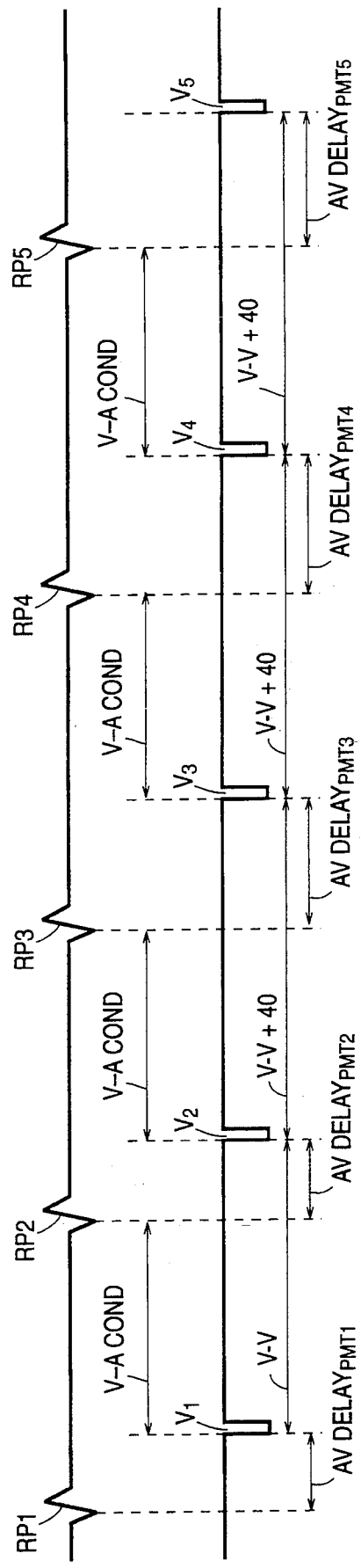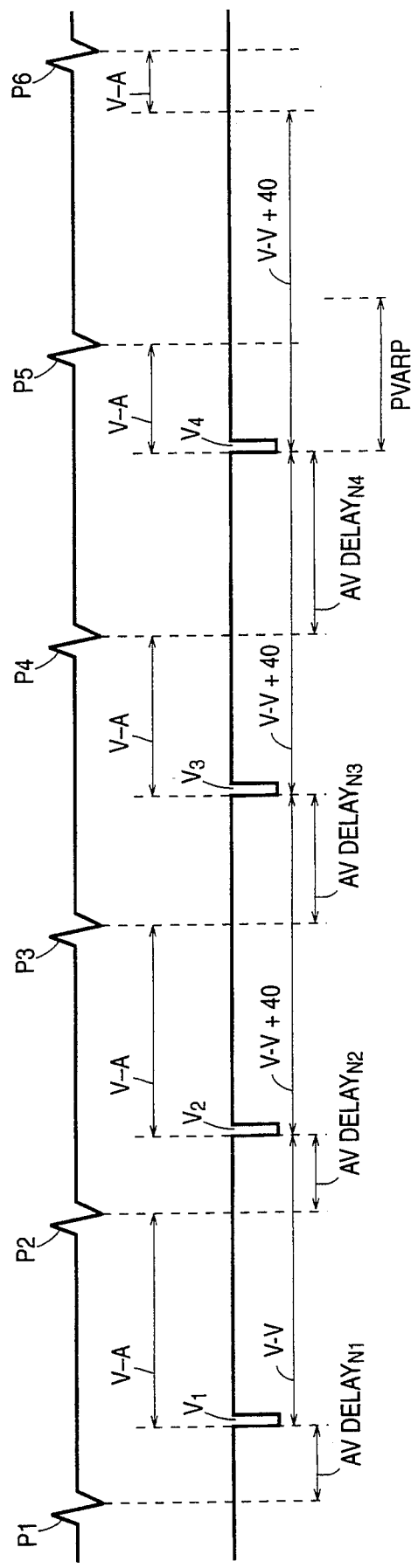

DUAL CHAMBER PACEMAKER WHICH DETECTS, CONFIRMS AND TERMINATES PACEMAKER MEDIATED TACHYCARDIA

FIELD OF THE INVENTION

This invention relates to dual chamber pacemakers and, more particularly, to dual chamber pacemakers that detect pacemaker mediated tachycardia and terminate it.

BACKGROUND OF THE INVENTION

Pacemaker mediated tachycardia (PMT) is a problem in conventional pacemakers that operate in an atrial synchronous pacing mode (e.g., DDD). If the patient's heart has retrograde conduction pathways (i.e., from the ventricle to the atrium) and there is a ventricular event at the opportune time (e.g., a premature ventricular contraction), a PMT can be established. The ventricular event is conducted to the atrium where it is sensed by the atrial channel of the pacemaker as if it were an inherent atrial event, i.e., a P-wave. This sensed atrial event initiates an A-V Delay and a ventricular pacing pulse. The resulting ventricular depolarization (V-pace) is retrogradely conducted to the atrium, and so a repetitive cycle is established. If the retrograde conduction time is consistent, then the ventricular pacing rate is determined by the sum of the A-V Delay and the retrograde conduction time.

The earliest dual chamber pacemakers attempted to solve the problem of pacemaker mediated tachycardia by limiting the ventricular pacing rate to a predetermined maximum rate. Unfortunately, such a ventricular rate limitation precludes a patient from realizing the advantages of atrioventricular (A-V) synchrony under circumstances when an elevated heart rate and A-V synchrony would be most beneficial, such as when exercising. One prior art technique allowing A-V synchronous pacing at higher atrial rates is to extend the A-V intervals for a number of pacing cycles, during which the ventricular pacing rate is not allowed to exceed the maximum rate. If a ventricular pace is scheduled which would cause the ventricular rate to surpass the maximum rate, it is skipped and, in the next cardiac cycle, the pacemaker reverts to A-V synchronous operation. A disadvantage of this procedure is that it carries the risk of creating excessively long actual A-V interval times which may themselves lead to PMT, particularly when the maximum rate is set to a relatively low value.

A common method for preventing PMT in an A-V synchronous pacemaker is to lengthen the atrial refractory period, also called the post ventricular atrial refractory period (PVARP). A disadvantage of this procedure is that it reduces the upper heart rates to which the pacemaker may respond synchronously. This procedure may be modified so that the PVARP is extended only when the probability of a retrograde VA transition is high, such as, for example, following a premature ventricular contraction (PVC). A PVC is a ventricular heartbeat which does not follow an atrial event. Unfortunately this may lead to a continued failure of P-wave sensing. Furthermore, an extension of the PVARP does not guarantee that a PMT will be terminated.

Several procedures have been advanced for automatically adjusting PVARP durations to avoid PMT, but yet to maintain an adequate upper rate response in a dual chamber pacemaker. U.S. Pat. No. 5,102,820 for "VDD Pacemaker with Selectable Post-Ventricular Atrial Refractory Periods", issued Apr. 14, 1992 to H. T. Markowitz, and U.S. Pat. No. 5,123,412 for "Dual-Chamber Pacemaker with Automatic Selection of Atrial Refractory Periods", issued Apr. 14, 1992 to R. A. Betzold, disclose pacemakers which prevent PMT by setting the PVARP duration as a function of whether the ventricular pacing pulse is triggered by the expiration of the A-V interval or by the expiration of the lower rate interval. A relatively short PVARP (e.g., 250 ms) is triggered by expiration of the A-V interval. Expiration of the lower rate interval is followed by a longer PVARP (e.g., 400 ms). The shorter PVARP following an A-V interval expiration is not likely to induce retrograde conduction because it is closely preceded by an atrial contraction. The longer PVARP following lower rate timeout prevents ventricular pacing pulses, which are not triggered in response to sensed atrial contractions, from inducing PMTs.

U.S. Pat. No. 5,129,393, entitled "Dual Chamber Rate Responsive Pacemaker with Variable Refractory Period" and issued Jul. 14, 1992 to D. A. Brumwell, prevents PMT by setting PVARP duration as a function of both a physiological sensor-determined ventricular pacing rate and the natural atrial rhythm. The sensor-determined ventricular rate is intended to correlate to a patient's metabolic demand. At low metabolic demand levels and atrial rates, the PVARP is lengthened to prevent premature atrial contractions from triggering ventricular pacing pulses. Therefore, the pacemaker tracks physiologically-appropriate rapid atrial rates in the presence of a low metabolic demand by following a gradual increase in intrinsic atrial rate with a gradual decrease in PVARP duration. Conversely, the pacemaker responds to a high metabolic demand in combination with a low intrinsic atrial rate by shortening the PVARP, allowing ventricular synchrony with appropriately timed natural atrial contractions. When the PVARP duration is short is the most likely condition for triggering PMT. Therefore, the pacemaker should be programmed to assure that an average atrial rate based on retrograde P-waves is not effective to maintain PMT.

A method and apparatus for detecting PMT is taught in U.S. Pat. No. 4,569,350, entitled "System For Detecting Pacer Mediated Tachycardia", issued to V. E. Mumford et al. on Feb. 11, 1986. Atrial P-waves and ventricular R-waves are sensed. When a P-wave is sensed, after a predetermined A-V Delay, a stimulating pulse is provided to the ventricle if no R-wave is sensed during the A-V Delay. A threshold rate is selected for the sensed P-P interval. If the ventricle has been stimulated and the threshold rate is exceeded for a selected number of cardiac cycles, the A-V Delay is increased by a predetermined time, delta. A determination is then made whether the next P-P interval has increased by delta. If so, a phenomenon termed "A-V precession" or simply "precession", then this is an indication that PMT has occurred.

The previously discussed procedures of limiting ventricular pacing rate and adjusting PVARP durations operate to prevent PMT at the expense of maintaining A-V synchrony when a patient is experiencing a high metabolic demand. Another procedure for dealing with PMT, which provides for an improved upper rate response in a pacemaker, is to maintain a short PVARP duration but to detect and treat PMT when it occurs. For example, in U.S. Pat. No. 4,554,921, entitled "Dual Chamber Pacemaker With Automatic High Rate Limit Mode Determination" and issued Nov. 26, 1985, W. Boute et al. discloses a method for monitoring retrograde P-waves and avoiding pacemaker mediated tachycardia, if possible. If avoiding PMT is not possible, the pacemaker detects and terminates PMT. The Boute et al. pacemaker does this by monitoring V-A stability. The V-A interval may be indicative of the retrograde conduction time for propagating cardiac depolarization from the ventricles to the atria. From the V-A stability, the pacemaker detects retrograde P-waves and PMT. The pacemaker breaks up PMT by skipping a ventricular stimulus which would normally be delivered in synchronous response to a sensed P-wave.

Another procedure is to avoid inducing PMT when it is most likely to occur. When a pacemaker switches from a VVI to a DDD mode, there is a substantial risk that synchronization will start precisely at the moment an atrial depolarization is triggered by a retrograde transition, and thus will initiate a pacemaker mediated tachycardia. Therefore, U.S. Pat. No. 4,802,483, entitled "Heart Pacemaker For Avoiding Pacemaker Mediated Tachycardia at Mode Switching" issued Feb. 7, 1989 to A. Lindgren, discloses a pacemaker which is intended to switch between VVI and DDD modes without causing PMT, while retaining good upper rate operation. Lindgren does this by determining a heart condition appropriate for switching to the atrial synchronous mode, and then delaying the transition to the atrial synchronous mode until the second (or later) atrial signal following the ventricular event, so that the first atrial signal does not trigger stimulation in the atrium. Therefore, the second atrial signal cannot have been produced by the retrograde transition of a ventricular signal, but rather it is representative of a heartbeat of true atrial origin. If no atrial signals are forthcoming, the pacemaker waits a predetermined delay interval (e.g., 200 ms or a programmable duration) and begins pacing in A-V synchrony.

In U.S. Pat. No. 5,085,215, entitled "Metabolic Demand Driven Rate-Responsive Pacemaker" and issued on Feb. 4, 1992, T. A. Nappholz et al. describe a pacemaker that automatically selects an appropriate pacing mode, either DDDR or VVIR, based on an analysis of a patient's natural atrial rate and its relationship with a metabolic indicator rate derived from the output of a physiological sensor. This pacemaker compares the sensed natural atrial rate to a "maximum rate for synchronous pacing", which is a function of the derived metabolic indicator rate, to classify an atrial rhythm as physiological or pathological. The upper rate response mechanism of this pacemaker provides for A-V synchrony at natural sinus rates ranging from low rates to high exercise rates, even up to the programmed maximum rate, but maintains ventricular rate stability during pathological atrial tachycardias by reverting to pacing in a rate-responsive VVI mode.

A PMT may drive the atrial heart rate at varying speeds, including fast pathological rates and slower physiological rates that may arise when a patient exercises. The retrograde conduction times which give rise to a PMT may be constant or irregular. It is an objective of the present invention to detect, confirm and terminate PMT, whether the atrial rates are pathological or physiological, regardless of the regularity of retrograde conduction. (The invention tests for the PMT condition continuously, confirms PMT rarely, and executes the PMT termination procedure even less frequently.)

SUMMARY OF THE INVENTION

In accordance with the principles of our invention, in the illustrative embodiment thereof, there are two stages of PMT detection and a termination procedure. The first level of detection is a check on the stability of a fast sensed atrial rate. The check is done continuously and has no effect on the operation of the pacemaker timing cycles. If the atrial rate is stable (within a programmed limit, say 3%), then the next stage of detection, confirmation, is initiated.

Confirmation has a slight effect on the pacemaker timing because it temporarily reprograms the ventricular tracking limit (otherwise known as the maximum rate) to a value just below the stable atrial rate, e.g., 5 ppm or a 40-ms extension to the V-V interval).

If the sensed atrial events originate in the atrium, then increasing A-V prolongation from cycle to cycle will occur due to well-known Wenckebach behavior. This is because the pacemaker is attempting to maintain A-V synchrony, without exceeding the ventricular tracking limit.

If the atrial senses are due to retrograde conduction, however, their rate equals the ventricular pacing rate, so there will be a constant increase in the A-V Delay, unlike Wenckebach behavior. If this occurs, PMT is confirmed and the termination sequence is initiated.

The termination procedure makes the atrium and the AV node refractory with an atrial pace, over-riding the usual pacemaker sequence. Following the atrial sense after PMT confirmation, an Atrial Protection Interval (API) is timed, an atrial pace is issued, and there follows an A-V Delay and a ventricular pace (unless inhibited by an R-wave).

BRIEF DESCRIPTION OF THE DRAWINGS

Further objects, features and advantages of the invention will become apparent upon consideration of the following description, taken in conjunction with the accompanying drawing, in which:

FIG. 3 is a timing diagram for a number of cardiac cycles illustrating the operation of the pacemaker of FIG. 1 during the confirmation procedure in the presence of PMT;

FIG. 4 is a timing diagram for a number of cardiac cycles illustrating the operation of the pacemaker of FIG. 1 during the confirmation procedure in the presence of sinus P-waves.

DETAILED DESCRIPTION OF THE INVENTION

Figure 1:
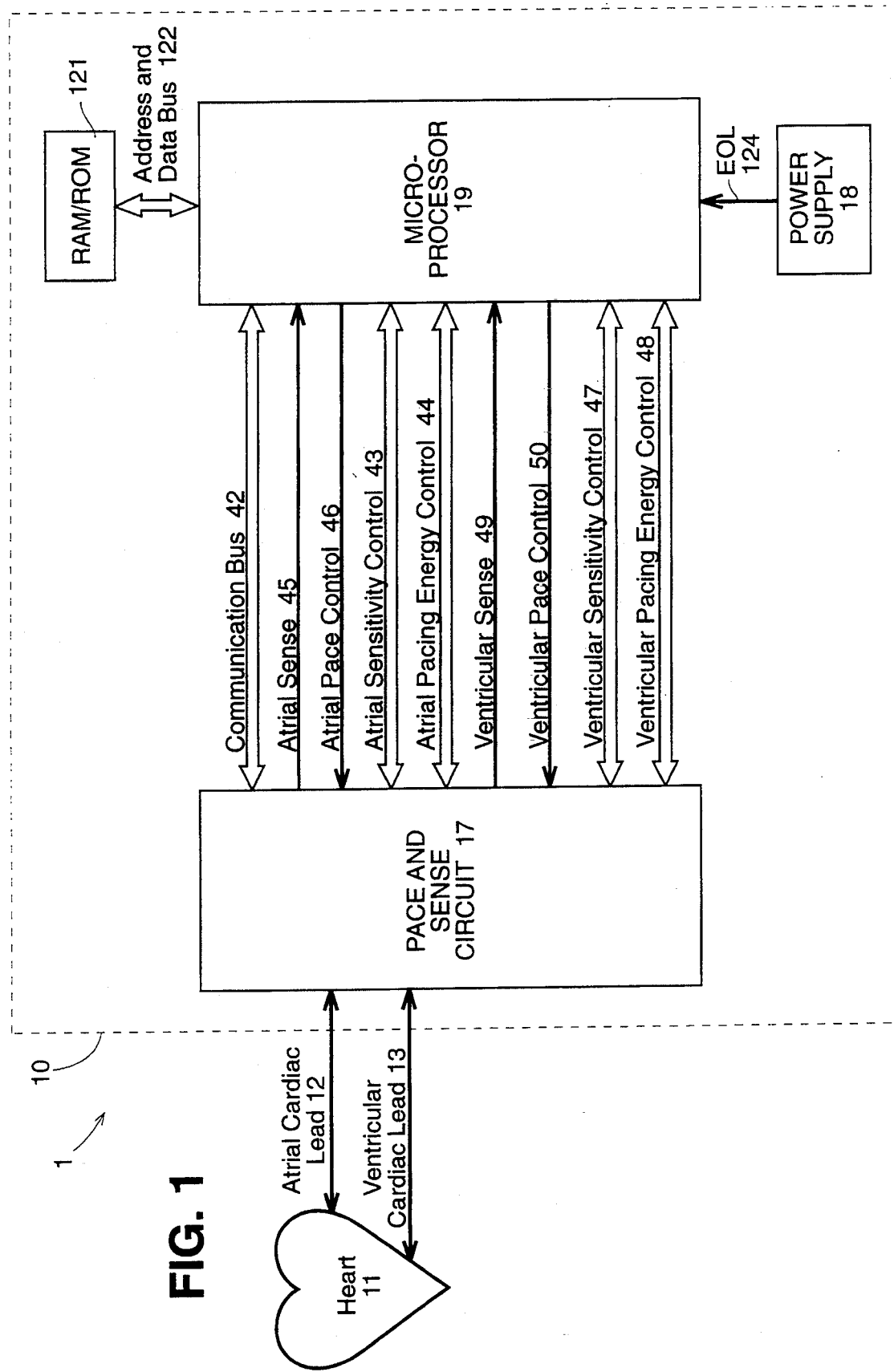
FIG. 1 is a block diagram of a rate-responsive, dual chamber pacemaker which embodies the subject invention.
Figure 2:
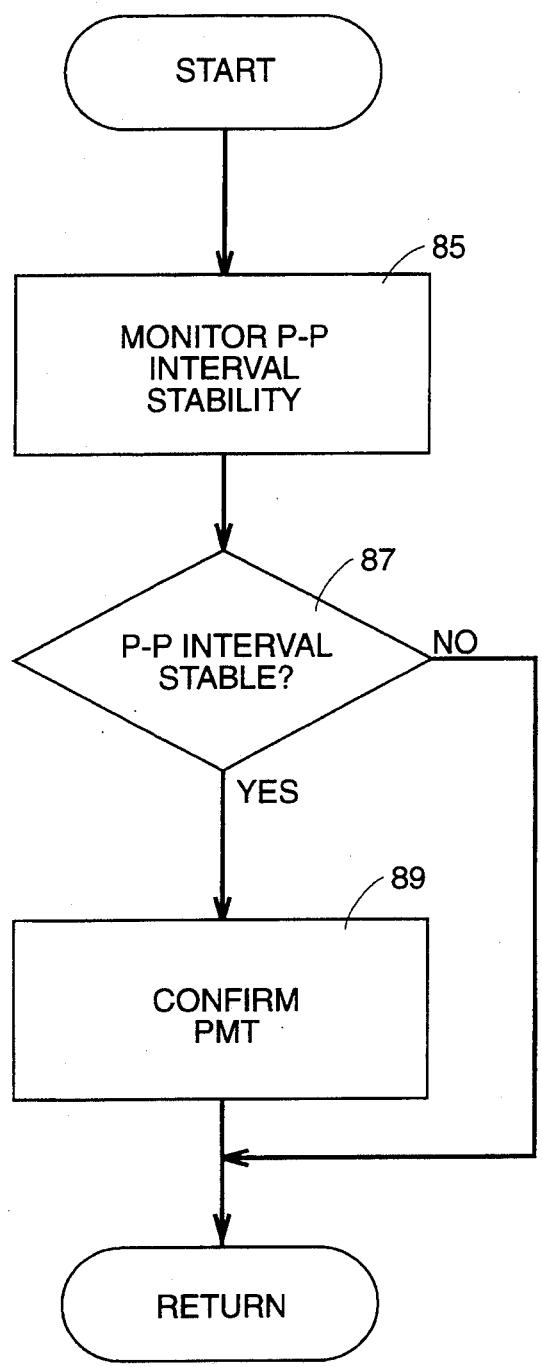
FIG. 2 illustrates the logic flow of the PMT detection and confirmation.

An illustrative pacemaker in which the subject invention may be implemented is disclosed in the co-pending application of Tibor A. Nappholz entitled "Forced Atrioventricular Synchrony Dual Chamber Pacemaker", filed on even day herewith and assigned to the assignee of the subject application. FIG. 1 herein is the same as FIG. 1 in the Nappholz application. The only difference is that while in the Nappholz drawing the pace and sense circuit 17 is shown as being represented in detail in FIG. 2 and microprocessor 19 is shown as being represented in detail in FIG. 3, those indications are not included on FIG. 1 herein. FIGS. 1 and 2 of the Nappholz application provide details of pace and sense circuit 17, and microprocessor 19, and the Nappholz application, incorporated by reference, completely depicts a pacemaker in which the subject invention may be employed. For the purposes of the subject invention, however, it is sufficient to understand just the block diagram of FIG. 1.

The pacemaker 1 is designed to be implanted in a patient and includes a pulse generator 10 and appropriate leads for electrically connecting the pulse generator to the patient's heart 11. The pacemaker includes atrial and ventricular cardiac leads 12 and 13 extending to the patient's heart for the administration of pacing therapy to the atrium and ventricle. The pulse generator 10 includes a pace and sense circuit 17 for the detection of analog signals representing cardiac electrical activity and for the delivery of pacing pulses to the heart; a microprocessor 19 which, in response to numerous inputs received from the pace and sense circuit 17, performs operations to generate different control and data outputs to the pace and sense circuit 17; and a power supply 18 which provides a reliable voltage level to the pace and sense circuit 17 and the microprocessor 19 by electrical conductors (not shown).

The microprocessor 19 is connected to a random access memory/read only memory unit 121 by an address and data bus 122. An end-of-life signal line 124 is used to provide, to the microprocessor 19, a logic signal indicative of the approach of battery failure in the power supply 18. The microprocessor 19 and the pace and sense circuit 17 are connected by a communication bus 42, an atrial sense line 45, an atrial pace control line 46, an atrial sensitivity control bus 43, an atrial pacing energy control bus 44, a ventricular sense line 49, a ventricular pace control line 50, a ventricular sensitivity control bus 47, and a ventricular pacing energy control bus 48.

It will be apparent to those skilled in the art that the principles of the subject invention may be applied to any conventional dual-chamber pacemaker. It is therefore to be understood that the system of FIG. 1 is only representative, and that even the full disclosure to be found in the Nappholz application is only illustrative.

The pacemaker operates by dividing each cycle into four well known sequential phases—AV Delay, PVARP, API and Alert. These phases are described in the Nappholz application and will not be repeated herein. The present invention is directed to an improved operation by the addition of the PMT detection and termination function which overcomes the limitations of restricted maximum rates as a result of long PVARP intervals.

FIG. 2 illustrates the logic flow of the PMT detection and confirmation. A monitor routine (step 85) checks if the P-P intervals are stable in the Alert interval; only if they are stable is PMT suspected. Also, PMT is suspected only if the rate of a predetermined number of atrial events (e.g., four) is above a threshold value, e.g., 100 beats per minute.

Since a PMT is due to retrograde conduction arising from ventricular pacing pulses, stability over a number of cycles of the sensed P waves is a property of PMT. The stability of P-P intervals is monitored (step 85) without affecting the pacemaker timing cycle.

The stability monitor is simple. The P-P intervals of 32 successive atrial senses are stored. The 16 oldest intervals are averaged together, and the 16 newest intervals are averaged together. If the two averages are within a programmed limit (e.g., 3%), then PMT is suspected (step 85) and confirmation (step 89) takes place. If the averages are different by more than the limit, the oldest interval is discarded, the next interval is stored, and the two averages are computed and compared. (No claim is made herein to invention in the stability check. The various Chorus pacemakers of ELA Medical detect ("suspect") PMT by using similar criteria, including verifying that in 8 consecutive cycles P-waves are followed by V-paces, the ventriculo-atrial (VP) intervals are less than 453 ms, and the VP intervals are stable within a limit of 31 ms. See, e.g., the Physician's Manual for the Chorus II pacemaker, p. 23.)

Confirmation of a PMT first requires modifying the values of the API and Alert intervals (in accordance with the usual rules) in order to decrease the ventricular tracking limit (maximum rate) to a rate slightly below the average intrinsic rate that has just been measured (e.g., 40 ms, or the interval corresponding to 5 ppm). FIG. 3 illustrates the resultant timing for a PMT.

Starting with the second cycle (it is assumed that stability is verified during the first), the minimum V-V interval (which was equal to the P-P interval) is extended by 40 ms. If PMT exists, then for each V-pace, there is a constant V-A (retrograde) conduction time. Since the V-A and A-V Delay intervals add up to the V-V interval, the A-V Delay is prolonged by the amount that the V-V interval was increased - 1:1 A-V synchrony is maintained, and all A-V Delays are increased by the same 40 ms and are constant. (It is because the V-V and V-A intervals are constant for a PMT condition that the increase in V-V is necessarily reflected in A-V.) In FIG. 3, the subscripts PMT1, PMT2, etc. simply refer to the A-V Delay intervals in successive cycles in the presence of PMT. The P-waves are labeled RP to indicate that they are retrograde in origin. The V-A intervals are labelled "V-A COND" to indicate that ventricular beats are retrogradely conducted to the atrium. It should be noted that the P-wave intervals in FIG. 3 lengthen. This is because each P-wave interval is the sum of an A-V Delay and a V-A conduction interval, and the A-V Delay has been increased.

FIG. 4 illustrates the resultant timing for sinus P-waves. The subscripts N1, N2, etc. refer to successive cycles with sinus P-waves. The atrial rate is now shown as constant since there is no PMT. Because the P-waves are faster than the maximum ventricular rate (the tracking limit), there is progressive lengthening of the A-V Delay. This is conventional Wenckebach behavior - the ventricular tracking limit (V-V+40) determines when a V-pace can occur, thus stretching all A-V Delays. Because the P-P intervals are shorter than the V-V intervals, and both are fixed in duration, the A-V Delays necessarily get progressively longer. Eventually a P-wave falls in the PVARP (shown in cycle 5) and is untracked, i.e., Wenckebach behavior is exhibited.

The confirmation of a PMT is made if the A-V Delay lengthens by an amount approximately equal to the interval extension for three consecutive cycles (cycles 3-5 in FIG. 3). Conversely, if the A-V Delay progressively lengthens on each cycle, then a PMT is not in progress (FIG. 4). Monitoring of the A-V Delay is useful for determining PMT because even an unstable PMT is unlikely to regularly increment the A-V Delay. (With reference to the Chorus pacemaker referred to above, confirmation involves changing the A-V Delay and seeing its effect on the intervals between V-paces and succeeding P-waves.)

Figure 5:
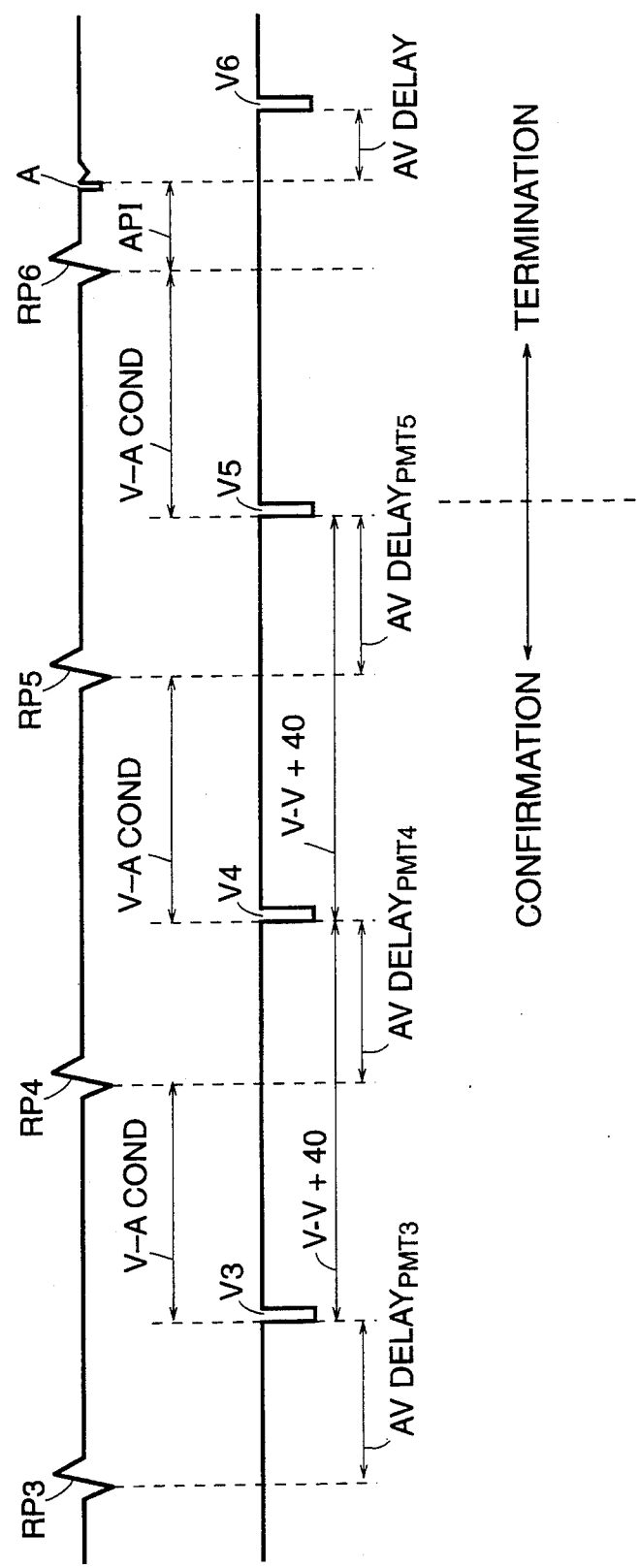
FIG. 5 is a timing diagram extension of FIG. 3 and illustrates the termination procedure.

Termination of the PMT is accomplished after it has been confirmed) by an extension of one cycle. FIG. 5 is a continuation of FIG. 3 and illustrates the resultant timing. In the cycle following confirmation, the API interval is timed and an atrial pace is delivered. The A-V Delay is then timed and a ventricular pace issued, unless inhibited by an R wave. The V-V interval is extended if necessary, thus preventing a V-pace from being generated as it ordinarily would be, i.e., for a single cycle the maximum rate of the pacemaker is decreased. Preferably, the shortest possible A-V Delay is used. A retrogradely conducted P-wave is most likely to occur while the atrium is still refractory from the A-pace, thus breaking the PMT. The reason for the introduction of an API is that the A-pace which is necessary (to make the atria refractory) should not compete with an unsensed P-wave —the usual non-competition rule. Introducing an API insures that there is no competition.

No claim is made herein to invention in the termination procedure by itself. It is a common technique to terminate PMT by extending the PVARP. (See, e.g., p. 26 of the above-identified Chorus manual.) The idea is to have the atrial channel ignore a P-wave so that an A-pace is generated. The resulting forced synchrony (A-pace followed by V-pace) may give rise to a retrogradely conducted P-wave, but it arrives when the SA node or atria are still refractory; another cycle does not ensue and the PMT is broken. Similarly, in the invention the PMT is broken by controlling a forced synchrony cycle.

If the test result is that there is no PMT, but rather just a fast sinus rate or supraventricular tachycardia, there is no termination phase. To prevent repeated executions of the test which would cause rate oscillation, the test may be inhibited from execution once again for a programmable number of cycles, e.g., 128 cycles.

Although the invention has been described with reference to a particular embodiment, it is to be understood that this embodiment is merely illustrative of the application of the principles of the invention. Accordingly, the embodiment described in particular should be considered exemplary, not limiting, with respect to the following claims.

What is claimed is:

1. A method of confirming the presence of pacemaker mediated tachycardia (PMT) following the initial detection thereof comprising the steps of:
   (a) measuring the intrinsic rate of the patient's heart,
   (b) adjusting the minimum V-V interval, corresponding to the maximum pacing rate of the pacemaker, to be slightly longer than the intrinsic interval corresponding to said measured rate,
   (c) determining whether the A-V Delay intervals in successive cycles progressively increase in Wenckebach fashion or remain constant, and
   (d) confirming the presence of PMT if the A-V Delay intervals in successive cycles remain constant.

2. A method in accordance with claim 1 wherein each pacemaker cycle includes sequential A-V Delay, PVARP, API and Alert intervals, and the steps for confirming the presence of PMT are performed only if a predetermined number of successive P-P intervals are stable.

3. A method in accordance with claim 2 wherein the steps for confirming the presence of PMT are performed only if a predetermined number of successive P-waves occur at a rate above a threshold value.

4. A method in accordance with claim 3 wherein, following the confirmation of PMT, the PMT is terminated by extending the V-V interval of the pacemaker and forcing an A-pace followed by a V-pace.

5. A method in accordance with claim 4 wherein said A-pace is generated following a P-wave but delayed sufficiently to avoid atrial competition.

6. A method in accordance with claim 5 wherein atrial competition is avoided by interposing an API interval between said P-wave and said A-pace.

7. A method in accordance with claim 1 wherein the steps for confirming the presence of PMT are performed only if a predetermined number of successive P-P intervals are stable.

8. A method in accordance with claim 7 wherein, following the confirmation of PMT, the PMT is terminated by extending the V-V interval of the pacemaker and forcing an A-pace followed by a V-pace.

9. A method in accordance with claim 8 wherein said A-pace is generated following a P-wave but delayed sufficiently to avoid atrial competition.

10. A method in accordance with claim 1 wherein, following the confirmation of PMT, the PMT is terminated by extending the V-V interval of the pacemaker and forcing an A-pace followed by a V-pace.

11. A method in accordance with claim 10 wherein said A-pace is generated following a P-wave but delayed sufficiently to avoid atrial competition.

12. A method in accordance with claim 11 wherein each pacemaker cycle includes sequential A-V Delay, PVARP, API and alert intervals, and atrial competition is avoided by interposing an API interval between said P-wave and said A-pace.

13. A dual-chamber pacemaker comprising means for generating atrial pacing pulses, means for generating ventricular pacing pulses, means for sensing atrial P-waves, means for sensing ventricular R-waves, and means for confirming the presence of pacemaker mediated tachycardia (PMT) following the initial detection thereof; said confirming means including means for measuring the intrinsic rate of the patient's heart, means for adjusting the minimum V-V interval, corresponding to the maximum pacing rate of the pacemaker, to be slightly longer than the intrinsic interval corresponding to said measured rate, means for determining whether the A-V Delay intervals in successive cycles progressively increase in Wenckebach fashion or remain constant, and means for confirming the presence of PMT if the A-V Delay intervals in successive cycles remain constant.

14. A pacemaker in accordance with claim 13 wherein each pacemaker cycle includes sequential A-V Delay, PVARP, API and Alert intervals, and said means for confirming the presence of PMT operates only if a predetermined number of successive P-P intervals are stable.

15. A pacemaker in accordance with claim 14 wherein said means for confirming the presence of PMT operates only if a predetermined number of successive P-waves occur at a rate above a threshold value.

16. A pacemaker in accordance with claim 15 further including means, operative following the confirmation of PMT, for terminating the PMT by extending the V-V interval of the pacemaker and forcing an atrial pacing pulse followed by a ventricular pacing pulse.

17. A pacemaker in accordance with claim 16 further including means for controlling said atrial pacing pulse to be generated following sensing of a P-wave but delayed sufficiently to avoid atrial competition.

18. A pacemaker in accordance with claim 17 wherein said controlling means operates to interpose an API interval between said P-wave and said atrial pacing pulse.

19. A pacemaker in accordance with claim 13 further including means, operative following the confirmation of PMT, for terminating the PMT by extending the V-V interval of the pacemaker and forcing an atrial pacing pulse followed by a ventricular pacing pulse.

20. A pacemaker in accordance with claim 19 further including means for controlling said atrial pacing pulse to be generated following sensing of a P-wave but delayed sufficiently to avoid atrial competition.

21. A pacemaker in accordance with claim 20 wherein each pacemaker cycle includes sequential A-V Delay, PVARP, API and Alert intervals, and said controlling means operates to interpose an API interval between said P-wave and said atrial pacing pulse.

* * * * *